United States Patent [19]

Shulgin

[11] 4,034,113
[45] July 5, 1977

[54] TREATMENT OF SENILE GERIATRIC PATIENTS TO RESTORE PERFORMANCE

[76] Inventor: Alexander T. Shulgin, 1483 Shulgin Road, Lafayette, Calif. 94549

[22] Filed: Apr. 15, 1976

[21] Appl. No.: 677,348

Related U.S. Application Data

[60] Division of Ser. No. 566,458, April 9, 1975, abandoned, which is a continuation-in-part of Ser. No. 304,069, Nov. 6, 1972, abandoned.

[52] U.S. Cl. .............................................. 424/330
[51] Int. Cl.$^2$ .................................... A61K 31/135
[58] Field of Search ................................... 424/330

[56] References Cited

UNITED STATES PATENTS

| | | | |
|---|---|---|---|
| 2,246,529 | 6/1941 | Nabenhauer | 260/570.8 |
| 3,457,354 | 7/1969 | Stone | 260/570.8 |
| 3,547,999 | 12/1970 | Shulgin | 260/570.8 |
| 3,655,737 | 4/1972 | Carlson et al. | 260/570.8 |
| 3,689,504 | 9/1972 | Horrom | 260/570.8 |

*Primary Examiner*—Stanley J. Friedman
*Attorney, Agent, or Firm*—Richard R. Lloyd

[57] ABSTRACT

Compounds of the formula

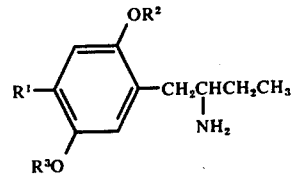

wherein $R^1$, $R^2$ and $R^3$ are alike or different and each is (lower)alkyl, including the racemic mixtures and the dextrorotatory and levorotatory isomers, and the pharmaceutically acceptable nontoxic salt thereof have been found to restore the performance of mammals, including man, and upon use in clinical studies in human geriatric patients have had a profound effect upon their mental alertness and attitudes without producing the undesirable stimulant side effects associated with the use of amphetamines.

11 Claims, No Drawings

TREATMENT OF SENILE GERIATRIC PATIENTS TO RESTORE PERFORMANCE

CROSS-REFERENCE TO RELATED APPLICATIONS

This application is a divisional application of copending Ser. No. 566,458 now abandoned, filed Apr. 9, 1975, which is a continuation-in-part of Ser. No. 304,069 filed Nov. 6, 1972 now abandoned.

BACKGROUND OF THE INVENTION

1. Field of the Invention

This invention relates to novel compounds which are useful for restoring the performance of mammals, including man, and they have been found to have a profound beneficial effect in human geriatric patients by increasing their mental alertness and improving their mental attitude and physical appearance without the undesirable side effects commonly associated with amphetamines, e.g., hypertension, tachycardia, anorexia, insomnia and post drug dysphoria.

In another aspect, this invention relates to a method of preparing the novel compounds. In still another aspect, this invention relates to a method of restoring the performance of mammals. In a further aspect, this invention relates to compositions useful in the method of restoring the performance capacity of mammals.

2. Description of the Prior Art

Numerous compounds structurally related to amphetamine (α-methylphenethylamine) have been prepared and reported in the literature and are the subject matter of various patents. Of particular interest with respect to the compounds disclosed herein are U.S. Pat. No. 3,547,999, Shulgin, A. T.: Chemistry and Structure-Activity Relationships of the Psychotomimetics which appeared in the book, Psychotomimetic Drugs, Ed. D. H. Efron, Raven Press 1970 and Shulgin, A. T., Sargen, T. and Naranjo, C.: Structure-Activity Relationships of One-Ring Psychotomimetics, Nature, 221:537 (1969). The foregoing patent and references disclose compounds closely related to the compounds of this invention. However, none of the compounds is disclosed as having the activity of the compounds of this invention. The Shulgin article in Psychotomimetic Drugs at pages 35–36 indicates that a "four chain compound" had been synthesized; however, the particular compound synthesized is not named, the structure is not disclosed, the method of preparation is not disclosed and no utility is disclosed in the article.

Other patents and publications reported from a search are U.S. Pat. No. 2,246,529; Journal of the American Chemical Society, Vol. 78, pages 4419–22 (1956); Journal of Medicinal Chemistry, Vol. 9, No. 4, pages 469–70 (1966); Arch. int. Pharmacodyn Vol. 154; No. 1., pages 26, 31–32 (1965); Chemical Abstracts, Vol. 61, page 6954a; Chemical Abstracts, Vol. 71, page 1278q; Chemical Abstracts, Vol. 67, pages 10215w; Chemical Abstracts, Vol. 72, page 1236w; and Chemical Abstracts, Vol. 59, page 3797d.

SUMMARY OF THE INVENTION

There is provided according to the present invention a pharmaceutical composition useful for restoring the performance of mammals which comprises an effective amount of a compound of the formula

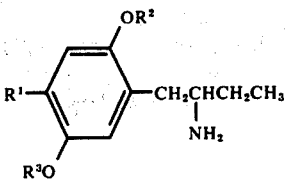

wherein $R^1$, $R^2$ and $R^3$ are alike or different and each is (lower)alkyl; or a pharmaceutically acceptable nontoxic salt thereof and a pharmaceutically acceptable carrier.

Another aspect of this invention is the provision of a method of restoring the performance of mammals, including man, which comprises administering to said mammal an effective amount, of a compound of formula I or a pharmaceutically acceptable nontoxic salt thereof.

A further aspect of this invention is the provision of a method of treating despondent, asocial, depressed, anxious and senile geriatric humans suffering from chronic organic brain disease and parkinsonism, which comprises administering to said humans an effective amount of a compound of formula I, or a pharmaceutically acceptable nontoxic salt thereof. The treatment of patients suffering the above-described symptoms results in the patients exhibiting near-normal behavior patterns.

The compounds of formula I contain an asymmetric carbon atoms and thus normally occur as a racemic mixture of the dextro- and levorotatory optical isomers. Both the dextro- and levorotatory isomers of these compounds, as well as the racemic mixtures are useful in the composition and method described above and are considered to be an integral part of the invention.

A further aspect of this invention is the provision of the dextro- and levorotatory isomers of the compounds of formula I; and the pharmaceutically acceptable nontoxic salts thereof.

The pharmaceutically acceptable nontoxic salts include the organic and inorganic acid addition salts, e.g., those prepared from acids such as hydrochloric, sulfuric, tartaric, fumaric, hydrobromic, hydriodic, glycolic, citric, maleic, phosphoric, succinic, acetic and the like. Such salts are prepared by conventional methods by reacting the free base with the desired acid on about an equivalent basis.

The term "(lower)alkyl" as used herein includes both straight chain and branched chain alkyl radicals containing from 1 to 4 carbon atoms, e.g., methyl, ethyl, propyl, isopropyl, butyl, sec-butyl, isobutyl and t-butyl.

A preferred embodiment of the instant invention is the compound having the formula

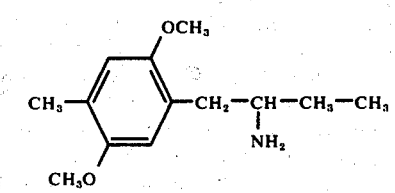

or a pharmaceutically acceptable nontoxic salt thereof.

A more preferred embodiment is the essentially pure dextrorotatory and levorotatory isomer of the compound having formula II supra.

The most preferred embodiment is the levorotatory isomer of compound II supra.

The compounds of formula I are prepared as exemplified below by reducing a 2-nitro-1-(2,5-(lower)-alkoxy-4-(lower)alkylphenyl)butene-1 of the formula

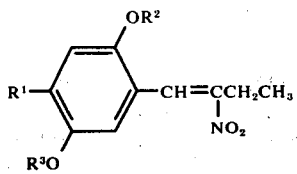

wherein $R^1$, $R^2$ and $R^3$ are as described above, with, for example, lithium aluminum hydride in the presence of a nonreactive solvent medium. Suitable solvents include diethyl ether, tetrahydrofuran, diethylene glycol dimethyl ether and the like. The reaction proceeds at temperatures from about 0° C. to 150° C. Preferably the reaction is carried out at the boiling temperature of the reaction mixture and under reflux and about 2 moles of lithium aluminum hydride per mole of butene are used. The preferred solvent is ether.

The general procedures for the preparation of the compounds of this invention and the starting materials are described in U.S. Pat. No. 3,547,999.

The racemic compounds of formula I may be resolved by forming a mixture of the two diastereoisomeric salts of said compounds with a dextrorotatory ring-substituted tartranilic acid, e.g., nitro, chloro bromo substituted, separating and diastereoisomeric salts by fractional crystallization and converting the separated distereoisomeric salts to the respective optical isomers of the compound preferably by treatment with a strong base, e.g., sodium carbonate, potassium carbonate and the like. (+)-2'-Nitrotartranilic acid and (+)-2'-chlorotartranilic acid are particularly useful in the resolution of the racemic compounds of Formula I. The general resolution procedure using tartranilic acids is described in U.S. Pat. No. 3,452,086 and by T. A. Montzka et al, J. Org. Chem. 33, 3993 (1968).

The compounds of formula I in the form of racemic mixtures or their dextrorotatory or levorotatory isomers possess performance restoring activity making them useful for enhancing the performance ability of mammals. The compounds while structurally related to amphetamine do not produce hypertension, tachycardia, anorexia, insomnia and post drug dysphoria which are common with amphetamine.

The performance restoration activity of the compounds of this invention was determined by the shuttle box acute acquisition, pole climb acute acquisition and pole climb chronic avoidance acquisition tests. Shuttle Box — Acute Acquisition Male hooded rats (500–700 gm.) were used as experimental subjects. The compounds are administered either subcutaneously or orally 30 minutes prior to shuttle box test. (shuttle box — manufactured by Lehigh Valley Electronics Co.). Each trial is 60 seconds long consisting of a 5 second avoidance period, during which the animal is required to move to the other side of shuttle box to avoid shock, and a 5 second shock period, if the animal fails to move during the avoidance period. During these 10 seconds, the cue light is lit on the other side of the test box but turned off if the animal moves to the other side of the box. The rate is given a maximum of 100 trails or until it acquires the ability to avoid 8 shocks out of 10 consecutive trials. Its score is the number of the trial which is the last trial prior to avoiding 8 shocks out of 10.

Pole Climb - Acute Acquisition

Male hooded rats (200 – 300 gms.) were used as experimental subjects. The compounds are administered subcutaneously 30 minutes prior to placement of the animal into the pole climb chamber (Cook, L., and Weidly, E. (1957), Ann. N.Y. Acad. Sci., 66, p. 740). Each trial is 60 seconds long consisting of a 5 second avoidance period, during which a sound is sounded and the animal has to jump up onto the pole and a 5 second shock period if the animal fails to jump. During the avoidance and shock periods the tone and electric shock are turned off if the animal jumps onto the pole. The animal is given a maximum of 100 trials or until it acquires the ability to avoid 8 shocks out of 10 consecutive trials. Its score is the number of the trial which is the last trial prior to attaining avoidance of 8 of 10 consecutive trials.

Pole Climb - Chronic Avoidance Acquisition

A similar procedure was used as in the pole climb-acute acquisition procedure described above but each animal was given 20 trials every day and the number of avoidances was determined. With each day there was an improvement in the performance; the number of avoidance responses increased.

When (±)-2-amino-1-(2,5-dimethoxy-4-methylphenyl)-butane hydrochloride and the dextrorotatory and levorotatory isomers were tested according to the foregoing procedures, the following results were obtained.

Table 1

Acute Avoidance Acquisiton by Breeder Rats in the Shuttle Box

| Compound | Dose (mg/kg) | No. of Animals | No. Trials required to reach 80% Avoidance |
| --- | --- | --- | --- |
| (+)-2-amino-1-(2,5-dimethoxy-4-methylphenyl)butane hydrochloride | 1 sc | 8 | 57 |
| | 5 sc | 10 | 58 |
| | 10 sc | 10 | 47 |
| | 10 po | 9 | 58 |
| (−)-2-amino-1-(2,5-dimethoxy-4-methylphenyl)butane hydrochloride | 1 sc | 9 | 65 |
| | 5 sc | 10 | 43 |
| | 10 sc | 9 | 39 |
| | 10 po | 7 | 66 |
| (±)-2-amino-1-(2,5-dimethoxy-4-methylphenyl)butane hydrochloride | 1 sc | 6 | 67 |
| | 10 sc | 8 | 37 |
| Saline | — | 20 | 85 |

Table 2

Acute Avoidance Acquisition by Adult Rat in the Pole Climb

| Compound | Dose (mg/kg sc) | No. of Animals | No. Trials Required to Reach 80% Avoidance |
| --- | --- | --- | --- |
| (+)-2-amino-1-(2,5-dimethoxy-4-methylphenyl)butane hydrochloride | 10 | 10 | 85 |
| (−)-2-amino-1-(2,5-dimethoxy-4-methylphenyl)butane hydrochloride | 10 | 10 | 65 |
| Saline | — | 10 | 100 |

Table 3

Chronic Avoidance Acquisiton by Adult Rats in the Pole Climb (12 Rats Used) No. Avoidances/240 Trials.

| Treatment Day | (+)-2-amino-1-(2,5-dimethoxy-4-methylphenyl)butane hydrochloride 5 mg/kg sc | (−)-2-amino-1-(2,5-dimethoxy-4-methylphenyl)butane hydrochloride 5 mg/kg sc | Saline |
|---|---|---|---|
| −1 | 17/240 | 18/240 | 20/240 |
| 1 | 56/240 | 63/240 | 51/240 |
| 2 | 76/240 | 85/240 | 63/240 |
| 3 | 91/240 | 108/240 | 77/240 |
| 4 | 103/240 | 101/240 | 94/240 |

The above test results disclose that the racemic mixture, (±)-2-amino-1-(2,5-dimethoxy-4-methylphenyl)butane hydrochloride, and the dextrorotatory and levorotatory isomers exhibit learning enhancing activity, the levorotatory isomer appeared to exhibit greater activity than th dextrorotatory isomer. No increase in locomotion activity was observed after administration of the racemic mixture or either of the isomers.

The ability of (−)-2-amino-1-(2,5-dimethoxy-4-methylphenyl)butane hydrochloride (BL-3912A) to restore performance in humans have been confirmed in the initial clinical trials.

(−)-2-amino-1-(2,5-dimethoxy-4-methylphenyl)butane hydrochloride has demonstrated remarkable and profound effects in initial clinical studies in senile geriatric patients. For example, in geriatric nursing home patients that were dull and presented varying degrees of inactivity and withdrawal, a dose of 100–300 mg. per day produced remarkable results. Mood and behavarior improved and patients became more alert, active and less disabled.

At similar doses a reduction in rigidity and tremor occurred in patients suffering from moderate to severe Parkinsonism. During BL-3912A therapy, handwriting, speech and feeding habits dramatically improved.

In one study involving 14 nursing home patients, improvement progressed to the point where the investigator felt some patients were well enough to return home.

The response to a particular dose level of the compound is variable and peculiar to each patient. In general, the patient should be titrated to his own needs.

In clinical trials BL-3912A did not produce hypertension, tachycardia, anorexia, insomnia and post drug dysphoria which are commonly seen following administration of amphetamine and other stimulants commonly used to restore performance, e.g., Ritalin and pemoline.

BL-3912A is devoid of hallucinogenic activity in mammals, including man and has been found to antagonize the effects of 2,5-dimethoxy-4-methyl-amphetamine (DOM) in rodents and cats. DOM is a hallucinogenic agent widely subjected to abuse by thrill-seeking youth and others.

The compounds of formula I may be administered as the free bases or in the form of their nontoxic addition salts. They may be compounded and formulated into pharmaceutical preparations in unit dosage form for oral or parenteral administration with organic or inorganic solid materials or liquids which are pharmaceutically acceptable carriers. Some examples of the carriers which can be used are gelatin capsules, sugars, cellulose derivatives such as carboxymethyl-cellulose, gelatin, talc, magnesium stearate, vegetable oil such as peanut oil, etc., liquid petroleum, glycerin, sorbitol, ethanol, agar, elixirs, syrups and water including sterile water. The composition may take the form of tablets, powders, granules, capsules, suspensions, solutions and the like.

The compounds of formula I when administered orally or parenterally in an effective amount restore performance in mammals. An oral dosage range of about 1 to about 5 milligrams per kilogram of body weight is a convenient dosage for producing these effects in mammals. However, in general, the particular dosage most suitable for a particular application, as might be expected, will vary with the age, weight and general health of the mammal under treatment and the degree of performance improvment present. After taking into consideration these factors and any other factors to be considered, one skilled in the art of treating diseases of mammals can readily determine the diseases of mammals can readily determine the appropriate dosage.

The compounds of formula I are administered orally or parenterally in the treatment of geriatric patients suffering from senility or parkinsonism in dosages of 25 to 100 mg. one to four times a day depending upon the effect desired. However, in general, the particular dosage most suitable for a particular application, as might be expected, will vary with the age, weight and general health of the human under treatment. One skilled in the art of treating human diseases can readily determine the appropriate dose for the respective patient.

The following examples are intended to illustrate the invention described herein without unduly restricting it.

EXAMPLE 1

Preparation of 2,5-Dimethoxytoluene

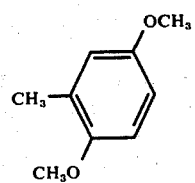

To a solution of 50 g. potassium hydroxide in methanol is added 50 g. of toluhydroquinone. The resulting solution is heated on a steam bath, and an excess of methyl iodide (75 ml.) is added through an effective reflux condenser. The addition is continued over several hours, and the resulting combination heated at reflux for several additional hours. At this time, the reaction mixture is brought to room temperature, acidified with hydrochloric acid, and exhaustively extracted with methylene chloride.

The organic phase of the above-extraction is washed with 5% sodium hydroxide solution (to remove all phenolic byproducts), then with water. The solvent remaining is concentrated by evaporation, yielding a residual neutral oil (36.9 g.). This upon distillation yielded 2,5-dimethoxytolunene as a pale amber liquid (b.p. 105°–111° C at 20 mm/Hg. The base washes yield, after acifification and extraction, 14.1 g. of a mixture of the two possible monomethylated derivatives which can be recycled in a subsequent repetition of the methylation step.

EXAMPLE 2

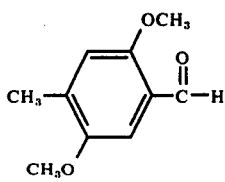

A solution of 40 ml. phosphorous oxychloride (POCl₃) and 45 ml. of N-methylformanilide is allowed to stand at ambient temperature for 50 minutes. There is then added 15.2 g. of 2,5-dimethoxytoluene and the resulting solution is heated on the steam bath for 140 minutes. The extremely dark viscous reaction mixture is added to 2 liters of water, and allowed to stir for several hours to complete the hydrolysis of the reaction intermediates. The solid product is removed by filtration, and after washing with water and air-drying yields 16.6 g of reddish crumbly crystals. This solid product is extracted with 2×125 ml. of boiling hexane, which on cooling deposits 12.1 g. of pale cream-colored crystals. Recrystallization from boiling hexane, yields a brilliant white product 2,5-dimethoxy-4-methylbenzaldehyde.

EXAMPLE 3

Preparation of
2-Nitro-1-(2,5-Dimethoxy-4-Methylphenyl)-Butene-1

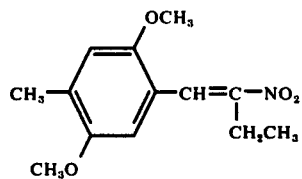

A mixture of 31.6 g. of 2,5-dimethoxy-4-methyl-benzaldehyde 20.2 ml. of nitropropane, 6 ml. cyclohexylamine, and 50 ml. benzene is kept at reflux in a Dean Stark apparatus for 24 hours. Cooling results in the spontaneous crystallization of an orange product, which on filtration and drying weigh 14.9 g. Recrystallization from methanol yields the product 2-nitro-1-(2,5-dimethoxy-4-methoxyphenyl)-butene-1 as an orange crystalline material, mp. 115° C.

EXAMPLE 4

Preparation of
(±)-2-Amino-1-(2,5-Dimethoxy-4-Methylphenyl) Butane

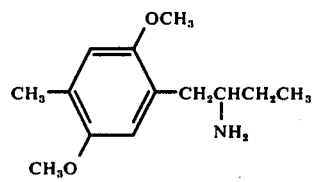

A suspension of 16 g. lithium aluminum hydride in 750 ml. anhydrous ether is brought to reflux, and through a Soxhlet thimble, 19.2 g. of 2-nitro-1-(2,5-dimethoxy-4-methylphenyl)butene-1 is added. The reflux is maintained for 24 hours, then the reaction mixture is cooled externally with ice, and 500 ml. of a 20% solution of sulfuric acid is added cautiously. The two phase result is separated, and the aqueous fraction washed with ether. To this fraction is added 400 g. potassium sodium tartrate and the pH adjusted with aqueous sodium hydroxide until greater than 9. The product is extracted with methylene chloride, which when removed leaves a clear, colorless oil, (±)-2-amino-1-(2,5-dimethoxy-4-methyl-phenyl-butane. This is dissolved in ether, and saturated with anhydrous hydrogen chloride. The crystalline hydrochloride of (±)-2-amino-1-(2,5-dimethoxy-4-methylphenyl)-butane thus obtained, after filtration and washing with additional anhydrous ether, weighed 12.0 g.

EXAMPLE 5

When in the procedure of Example 4, 2-nitro-1-(2,5-dimethoxy-4-methylphenyl)-butene-1 is replaced by an equal molar amount of 2-nitro-1-(2,5-dimethoxy-4-ethylphenyl)-butene-1,
2-nitro-1-(2,5-dimethoxy-4-propylenyl)-butene-1,
2-nitro-1-(2,5-dimethoxy-4-isopropylphenyl)-butene-1,
2-nitro-1-(2,5-dimethoxy-4-butylphenyl)-butene-1,
2-nitro-1-(2,5-diethoxy-4-methylphenyl)-butene-1,
2-nitro-1-(2,5-dipropoxy-4-methylphenyl)-butene-1,
2-nitro-1-(2,5-diisopropoxy-4-methylphenyl)-butene-1,
2-nitro-1(2,5-dibutoxy-4-methylphenyl)-butene-1,
2-nitro-1-(2-methoxy-5-ethoxy-4-methylphenyl)-butene-1,
2-nitro-1-(2-ethoxy-5-methoxy-4-methylphenyl)-butene-1,
2-nitro-1-(2,5-diethoxy-4-ethylphenyl)-butene-1, and
2-nitro-1(2,5-diethoxy-4-propylphenyl)-butene-1,
there are obtained
(±)-2-amino-1-(2,5-dimethoxy-4-ethylphenyl)-butane,
(±)-2-amino-1-(2,5-dimethoxy-4-propylphenyl)-butane,
(±)-2-amino-1-(2,5-dimethoxy-4-isopropylphenyl)-butane,
(±)-2-amino-1-(2,5-dimethoxy-4-butylphenyl)-butane,
(±)-2-amino-1-(2,5-diethoxy-4-methylphenyl)-butane,
(±)-2-amino-1-(2,5-dipropoxy-4-methylphenyl)-butane,
(±)-2-(2,5-diisopropoxy-4-methylphenyl)-butane,
(±)-2-amino-1-(2,5-dibutoxy-4-methylphenyl)-butane,
(±)-2-amino-1-(2-methoxy-5-ethoxy-4-methylphenyl)-butane,
(±)-2-amino-1-(2-ethoxy-5-methoxy-4-methylphenyl)-butane,
(±-2-amino-1-(2,5-diethoxy-4-ethylphenyl)-butane,
(±)-2-amino-1-(2,5-diethoxy-4-propylphenyl)-butane Resolution of
1-Amino-1-(2,5-dimethoxy-4-methylphenyl)-butane.

EXAMPLE 6

A.

(+)-2-Amino-1-(2,5-dimethoxy-4-methylphenyl)butane hydrochloride.

(±)-2-Amino-1-(2,5-dimethoxy-4-methylphenyl)butane (17.9 g., 80.2 mmoles) and 10.82 g. (40.1 mmoles) of (+)-2'-nitrotartranilic acid were dissolved in 5 ml. of hot 95% ethanol. The solution was cooled, seeded with salt previously obtained on a test tube scale, and allowed to stand undisturbed at room temperature (20°–25° C.) until crystallization was complete (at least 18 hours). The solid was filtered, sucked as free of mother liquid as possible, and washed with 10 ml. of cold (−15° C.) 95% ethanol in two portons. The mother liquid and washings were reversed for recovery of the (−)-isomer. The product was air-dried to give 12.32 g. of the pure (+)-2′-nitrotartranilic salt of (+)-2-amino-2-(2,5-dimethoxy-4-methylphenyl)butane, mp. 155.5°–157° C.

Anal. Calc'd. for $C_{23}H_{31}N_3O_9$: C, 55.97; H, 6.33; N, 8.52. Found: C, 55.63; H, 6.19; N, 8.43.

This salt was dissolved in 100 ml. of hot ethanol. The solution was cooled and poured into excess dilute potassium carbonate solution. The mixture was extracted with two portions of ether; the combined mixture was extracted with two portions of ether; the combined ether extracts were washed with dilute potassium carbonate solution, dilute sodium bicarbonate solution, and three portions of water. Drying and evaporations of the solvent gave 3.8 g. of pure (+)-2-amino-1-(2,5-dimethoxy-4-methyl-phenyl)butane as a light yellow oil which crystallized upon standing, $[\alpha]_{365}^{26} + 1.55.3°$ (c 1.273, 95% ethanol). The salt was formed with HCl gas in anhydrous ether. The solid was filtered, washed with ether and air-dried to give 4.34 g. of slightly yellowish powder. Recrystallization from 105 ml. of 2-propanol provided 3.70 g. of pure (+)-2-amino-1-(2,5-dimethoxy-4-methyl-phenyl)butane hydrochloride as colorless, fluffy needles, m.p. 245°–246° C., $[\alpha]_{375}^{23} + 49.8°$ (c 1.000, 95% EtOH). The overall yield was 35% of available (+)-isomer.

Anal. calc'd. for $C_{13}H_{21}NO_2 \cdot HCl$: C, 60.10; H, 8.54; N, 5.39; Cl, 13.65. Found: C, 59.79; H, 8.57; N, 5.18; Cl, 13.57.

B.
(−)-2-Amino-(2,5-dimethoxy-4-methylphenyl)butane-hydrochloride.

The mother liquor from isolation of the (+)-isomer was evaporated and the residue was converted to the free base as described above. The oil thus obtained and 9.37 g. (36.1 mmoles, 0.9 molar equiv.) of (+)-2′-chloro-tartranilic acid were dissolved in 85 ml. of hot 95% ethanol. The solution was cooled, seeded with salt previously obtained on a test tube scale, and allowed to stand undisturbed at room temperature until crystallization was complete (at least 18 hours). The solid was filtered, washed with 10 ml. of cold (−15°) 95% ethanol, and air-dried; 13.22 g. of light yellowish, fluffy crystals was obtained (76%). Two recrystallizations in a like manner from 10 ml./g. of 95% ethanol gave 7.99 g. (60% recovery) of pure, colorless (+)-2′-chlorotartranilic acid salt of (−)-2-amino-1(2,5-dimethoxy-4-methylphenyl)butane, m.p. 182.5°–184° C.

Anal. calc'd. for $C_{23}H_{31}ClN_2O_7$: C, 57.19; H, 6.47; N, 5.80; Cl, 7.34. Found: C, 56.91; H, 6.56; N, 5.90; Cl, 7.16.

This salt was converted to the free base as described for the (+)-isomer. Pure (−)-2-amino-1-(2,5-dimethoxy-4-methylphenyl)butane (3.6 g.) was recovered as an almost colorless oil which crystallized upon standing, $[\alpha]_{365}^{23.5} − 156.3°$ [c 1.274, 95% ethanol). The salt was formed with anhydrous HCl and the colorless powder (4.18 g.) thus obtained was recrystallized from 110 ml. of 2-propanol to give 3.64 of pure (−)-2-amino-1-(2,5-dimethoxy-4-methylphenyl)butane hydrochloride as colorless, fluffy needles, m.p. 245°–246° C., $[\alpha]_{365}^{24} − 49.9°$ (c 1.000 95% ethanol). The overall yield was 35% of available (−)-isomer.

Anal. calc'd. for $C_{13}H_{21}NO_2 \cdot HCl$: C, 60.10; H, 8.54; N, 5.39; Cl, 13.65. Found: C, 59.93; H, 8.70; N, 5.44; Cl, 13.73.

EXAMPLE 7

When in the procedure of Example 6 (±)-2-amino-1-(2,5-dimethoxy-4-methylphenyl)butane is replaced by an equimolar amount of each of the racemic compounds produced in Example 5, there is obtained the individual dextrorotatory and levorotatory isomers of each compound.

EXAMPLE 8

Tablets are prepared from the following formulations.

FORMULATIONS A

| | Per tablet, mg. |
|---|---|
| 2-amino-1-(2,5-dimethoxy-4-methylphenyl)butane hydrochloride | 10 |
| Cornstarch | 100 |
| Methylcellulose 400 | 175 |
| Magnesium stearate | 3 |
| Total | 288 |

Each tablet contains 10 mg. of active ingredient.

FORMULATION B

| | Per tablet, mg. |
|---|---|
| 2-amino-1-(2,5-dimethoxy-4-methylphenyl)butane hydrochloride | 10 |
| Monocalcium phosphate | 70 |
| Dicalcium phosphate | 70 |
| Lactose | 70 |
| Magnesium stearate | 3 |
| Total | 223 |

A mixture of monocalcium phosphate, dicalcium phosphate and lactose is prepared to which is added magnisium stearate and 2-amino-1-(2,5-dimethoxy-4-methylphenyl)butane hydrochloride and then tabletted by conventional means. Each tablet contains 10 mg. of active ingredient.

While this invention has been described and exemplified in terms of its preferred embodiment, those skilled in the art will appreciate that modifications can be made without departing from the spirit and scope of the invention.

I claim:

1. A method of treating senile geriatric humans to restore performance which comprises administering to said human an effective amount of a compound of the formula

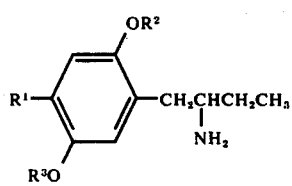

wherein R¹, R² and R³ are alike or different and each is (lower)alkyl; or a pharmaceutically acceptable non-toxic salt thereof.

2. The method of claim 1 wherein the compound administered has the formula

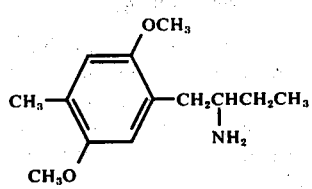

3. The method of claim 1 wherein the compound administered is a pharmaceutically acceptable non-toxic salt of the compound of the formula

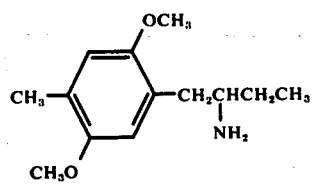

4. The method of claim 1 wherein the compound administered is the hydrochloric salt of the compound of the formula

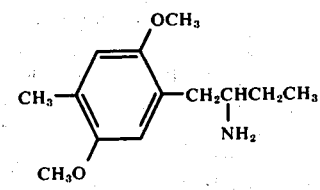

5. The method of claim 1 wherein the compound administered is (−)-2-amino-1-(2,5-dimethoxy-4-methylphenyl)butane.

6. The method of claim 1 wherein the compound administered is a pharmaceutically acceptable non-toxic salt of (−)-2-amino-1-(2-amino-1-(2,5-dimethoxy-4-methyl-phenyl)butane.

7. The method of claim 1 wherein the compound administered is (−)-2-amino-1-(2,5-dimethoxy-4-methylphenyl)butane hydrochloride.

8. The method of claim 1 wherein the compound administered is (+)-2-amino-1-(2,5-dimethoxy-4-methylphenyl)butane.

9. The method of claim 1 wherein the compound administered is a pharmaceutically acceptable non-toxic salt of (+)-2-amino-1-(2,5-dimethoxy-4-methyl-phenyl)butane.

10. The method of claim 1 wherein the compound administered is (+)-2-amino-1-(2,5-dimethoxy-4-methylphenyl)butane hydrochloride.

11. The method of claim 1 which comprises administering about 25 to about 100 milligrams per dose, one to four times a day.

* * * * *

UNITED STATES PATENT AND TRADEMARK OFFICE
CERTIFICATE OF CORRECTION

PATENT NO. : 4,034,113
DATED : July 5, 1977
INVENTOR(S) : Alexander T. Shulgin

It is certified that error appears in the above-identified patent and that said Letters Patent are hereby corrected as shown below:

Column 3, line 66, "rate" should read --rat--.
Column 3, line 67, "trails" should read --trials--.
Column 6, line 17, delete "diseases of mammals can readily determine the".

Column 8, line 19, "propylenyl" should read --propylphenyl--.
Column 9, line 1, "Eml." should read --85 ml.--.
Column 9, line 8, "reversed" should read --reserved--.
Column 9, line 25, "1.55.3°" should read --155.3°--.

Claim 4, line 2 thereof, "hydrochloric" should read --hydrochloride--.
Claim 6 should read
--The method of Claim 1 wherein the compound administered is a pharmaceutically acceptable nontoxic salt of (-)-2-amino-1-(2,5-dimethoxy-4-methylphenyl)butane--.

Signed and Sealed this

Eleventh Day of October 1977

[SEAL]

Attest:

RUTH C. MASON
Attesting Officer

LUTRELLE F. PARKER
Acting Commissioner of Patents and Trademarks